(12) United States Patent
Blake et al.

(10) Patent No.: US 10,850,088 B2
(45) Date of Patent: Dec. 1, 2020

(54) FLUID CONNECTOR WITH CLAMP AND PROTECTION

(71) Applicant: SARTORIUS STEDIM FMT SAS, Aubagne (FR)

(72) Inventors: Florian Blake, Hyeres (FR); Jeremy Gibelin, Le Beausset (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 381 days.

(21) Appl. No.: 14/901,545

(22) PCT Filed: Jun. 24, 2014

(86) PCT No.: PCT/FR2014/051577
§ 371 (c)(1),
(2) Date: Dec. 28, 2015

(87) PCT Pub. No.: WO2014/207368
PCT Pub. Date: Dec. 31, 2014

(65) Prior Publication Data
US 2016/0151620 A1 Jun. 2, 2016

(30) Foreign Application Priority Data
Jun. 28, 2013 (FR) .................................. 13 56350

(51) Int. Cl.
*F16L 33/025* (2006.01)
*A61M 39/28* (2006.01)
(Continued)

(52) U.S. Cl.
CPC ........ *A61M 39/28* (2013.01); *A61M 39/1011* (2013.01); *A61M 39/12* (2013.01);
(Continued)

(58) Field of Classification Search
CPC ......... F16L 33/228; F16L 33/10; F16L 33/20; F16L 33/32; F16L 33/207; F16L 33/24;
(Continued)

(56) References Cited

U.S. PATENT DOCUMENTS 2,008,650 A * 7/1935 Weatherhead, Jr. .. F16L 33/207
285/140.1
2,530,700 A * 11/1950 Jewell .................... F16L 21/005
285/236
(Continued)

FOREIGN PATENT DOCUMENTS

DE 737 252 7/1943
DE 103 47 927 5/2005
(Continued)

OTHER PUBLICATIONS

International Search Report dated Oct. 28, 2014, corresponding to PCT/FR2014/051577.

*Primary Examiner* — Aaron M Dunwoody
(74) *Attorney, Agent, or Firm* — Nixon & Vanderhye (57) ABSTRACT

A fluid-connection device capable of and intended for connecting a flexible pipe to a flexible or rigid pipe or enclosure in a biopharmaceutical assembly such as to provide fluid communication between two fluid spaces, including a first connector in fluid communication with the first fluid space, a second connector in fluid communication with the second fluid space, the first connector and the second connector optionally being coupled together in a coupling position, the first connector including a tubular nozzle which can be inserted in one end of the pipe, a pipe clamp being arranged around the end of the tube in order to clamp the pipe onto the tubular nozzle of the first connector, the second connector including protection elements which, in the coupling position, are positioned radially at least partially opposite (Continued)

the pipe clamp, whereby the pipe clamp cannot come into direct contact with external elements.

19 Claims, 5 Drawing Sheets (51) Int. Cl.
| | |
|---|---|
| *A61M 39/10* | (2006.01) |
| *F16L 33/22* | (2006.01) |
| *F16L 37/098* | (2006.01) |
| *A61M 39/12* | (2006.01) |
| *F16L 37/084* | (2006.01) |
| *A61J 1/14* | (2006.01) |

(52) U.S. Cl.
CPC ........... *F16L 33/025* (2013.01); *F16L 33/227* (2013.01); *F16L 37/084* (2013.01); *F16L 37/0987* (2013.01); *A61J 1/1481* (2015.05); *A61M 2039/1027* (2013.01); *A61M 2039/1066* (2013.01); *A61M 2205/6072* (2013.01); *F16L 33/221* (2013.01); *F16L 2201/44* (2013.01)

(58) Field of Classification Search
CPC ......... F16L 33/02; F16L 47/005; F16L 47/06; F16L 47/12; F16L 47/18; F16L 47/26; F16L 47/30
USPC ......... 285/241, 252, 253, 238, 80, 114, 115, 285/116, 256, 257, 258, 399, 400
See application file for complete search history.

(56) References Cited

U.S. PATENT DOCUMENTS

| | | | | |
|---|---|---|---|---|
| 2,877,437 | A * | 3/1959 | Flanagan, Jr. | H01R 13/6277 439/353 |
| 2,899,217 | A * | 8/1959 | Ashbrook et al. | F16L 33/32 285/105 |
| 3,030,130 | A | 4/1962 | Appleton | |
| 3,347,566 | A * | 10/1967 | Nelson | F16L 55/1007 285/1 |
| 3,463,517 | A * | 8/1969 | Jeromsom, Jr. | F16L 33/02 285/253 |
| 3,578,360 | A * | 5/1971 | Eliot | F16L 47/005 285/256 |
| 3,586,354 | A * | 6/1971 | Boscacci | F16L 21/005 285/339 |
| 3,784,236 | A * | 1/1974 | Slocum | F16L 33/224 285/45 |
| 3,971,577 | A * | 7/1976 | Schemith | F16L 19/14 285/238 |
| 4,049,034 | A | 9/1977 | Vcelka et al. | |
| 4,114,929 | A * | 9/1978 | Knapp | F02M 55/02 285/148.13 |
| 4,135,744 | A * | 1/1979 | Fouts | F16L 33/08 285/148.13 |
| 4,313,628 | A * | 2/1982 | Duenke | F16L 31/00 285/115 |
| 4,518,177 | A * | 5/1985 | Deakins | F16L 21/005 248/62 |
| 4,548,427 | A * | 10/1985 | Press | F16L 27/107 285/114 |
| 4,592,575 | A * | 6/1986 | Hughes | F16L 33/08 24/274 R |
| 6,779,269 | B2 * | 8/2004 | Green | F16L 35/00 285/114 |
| 2002/0000721 | A1 * | 1/2002 | Ohya | F16L 13/146 285/322 |
| 2007/0001453 | A1 | 1/2007 | Miyajima | |
| 2007/0170720 | A1 * | 7/2007 | Beatty | F16L 33/20 285/256 |
| 2007/0216158 | A1 * | 9/2007 | Kertesz | F16L 33/22 285/256 |
| 2012/0049512 | A1 * | 3/2012 | Hayes, Jr. | F16L 19/0283 285/256 |
| 2016/0146386 | A1 * | 5/2016 | Blake | A61M 39/1011 285/45 |
| 2017/0016564 | A1 * | 1/2017 | Berendsen | A01C 7/082 |

FOREIGN PATENT DOCUMENTS

| | | |
|---|---|---|
| DE | 10 2005 038439 | 2/2006 |
| EP | 2 497 989 | 9/2012 |
| FR | 2 385 971 | 10/1978 |
| FR | 2 769 350 | 4/1999 |

\* cited by examiner

FLUID CONNECTOR WITH CLAMP AND PROTECTION

FIELD OF THE INVENTION

The invention relates to fluid connectors, in particular for establishing fluid connections to couple a fluid-conveying pipe to another pipe or to a container, in the field of biopharmaceutical applications.

BACKGROUND OF THE INVENTION

Specifically, the tubes or pipes used in the biopharmaceutical field are flexible or highly flexible pipes which are used to convey various biopharmaceutical substances, most often with the aseptic precautions required.

In biopharmaceutical applications, this type of flexible pipe allows the circulation, passage, and communication of a fluid such as a biopharmaceutical fluid, and can either be connected to a similar flexible pipe or to a vessel or container which may be rigid or flexible.

The vessel or container in question may in this case be a container for storing and/or processing content such as a biopharmaceutical product. Such a container is in this case understood to mean a rigid or semi-rigid reusable container or a flexible disposable container such as a bag or possibly even a filter cartridge.

This bag may be one of the substantially thin "2D" bags, such as those marketed by Sartorius Stedim Biotech under the brand Flexboy®, having a typical volume of between 50 ml and 50 liters. This flexible bag may also be a "3D" bag, such as those marketed by Sartorius Stedim Biotech under the brand Flexel®, having a larger volume and a substantial size in all three dimensions. Note that a pipe such as the pipe of the invention can be placed between two bags or a larger number of bags.

A pipe of the invention, usually of circular cross-section, is typically made of a plastic such as silicone, thermoplastic elastomers (TPE), or PVC, although this list is not limiting. It has a certain general stability, and simultaneously both a certain overall flexibility and a certain local flexibility, which allows crimping the pipe or substantially deforming it radially when sufficient force is applied.

In a typical embodiment, for example, the pipe has an outer diameter between 8 mm and 30 mm for example, with the thickness depending on the material, the diameter, and the applications.

In the prior art, in order to couple such a flexible pipe, it is slipped over a tubular nozzle, whereupon a pipe clamp is placed around the pipe and the clamp is then tightened. The tightened clamp thus exerts a radial inward pressure to retain the flexible pipe on the nozzle, on the one hand to ensure a good seal between pipe and nozzle and on the other hand to prevent the pipe from detaching from the nozzle when pulled.

For such pipe clamps, a plastic clamp can be used for example, of polyamide for example such as Rilsan®. This type of plastic clamp, also sometimes called Serflex®, comprises a system of notches on a strip cooperating with a locking hook arranged in the head, such that the tightening is irreversible. In other words, after the strip is inserted into the head to form a loop, the strip is pulled to reduce the diameter of the loop and tighten the clamp; all return movement is prevented by the engagement of the hook in one of the notches of the strip. After tightening, to prevent the strip from projecting too far beyond the diameter of the clamp loop, the free portion of the strip is cut off close to the head of the clamp. The undetached remaining portion of the strip often has a sharp edge which can cut.

As an alternative to the plastic collar, a metal clamp can be used which is in the form of a preformed ring having one or two "ears" projecting outward with respect to the general shape of the ring of the clamp; this type of clamp is sometimes called an Oetiker® clamp. After placement of the clamp on the pipe to be retained, a tool is used to crimp the ear (or ears) of the clamp which causes a permanent deformation and thus a narrowing of the major diameter of the ring and as a result tightens the clamp on the pipe. This type of clamping with a metal ring is particularly robust and reliable. However, at the point where the ear was crimped by the tool, there may be a burr or roughness which forms a sharp edge that can be damaging.

Whether plastic or metal, once such clamps are installed in biopharmaceutical assemblies, these assemblies may need to be transported or moved and therefore there is a risk of damage by the damaging parts of these clamps to other elements of the biopharmaceutical assembly, particularly the flexible bags or flexible pipes, which can cause a leakage or loss of sterilization that is detrimental to the biopharmaceutical application.

In addition, these clamps are easy to access (and thus can be removed) and do not allow guaranteeing a satisfactory image or aesthetics.

There is therefore a need to propose an improvement that at least partially overcomes the aforementioned drawbacks of the known prior art.

OBJECTS AND SUMMARY OF THE INVENTION

A description of the invention as characterized in the claims is provided below.

According to a first aspect, the invention relates to a fluid-connection device adapted and intended for connecting a first wall defining a first fluid space, in the form of a flexible pipe, to a second wall defining a second fluid space, in the form of a flexible pipe or enclosure, for ensuring fluid communication between the first fluid space and the second fluid space, comprising:

a first connector defining a first hollow passage, adapted and intended for connection to the first wall and in fluid communication with the first space,
  a second connector defining a second hollow passage, adapted and intended for connection to the second wall and in fluid communication with the second space, the first connector and the second connector being adapted and intended to be coupled together in a relative coupling position, along an axis A,
the first connector comprising a tubular nozzle adapted and intended for insertion into one end of the pipe, and a front coupling portion,
  a pipe clamp adapted and intended for placement around the end of the pipe in order to clamp said pipe onto the tubular nozzle of the first connector,
the second connector comprising protective elements which, in the coupling position, are positioned so as to at least partially face the clamp in the radial direction, the protective elements being integrally formed from the body of the second connector.

The clamp thus cannot come into direct contact with external elements and thus prevents possible damage to nearby flexible bags or pipes by a damaging portion of the clamp.

In addition, the body of the second connector and the protective elements are advantageously and integrally obtained by a single economic molding operation.

In one embodiment, the protective elements are connected by flexible hinge areas to the body of the second connector; whereby the protective elements do not interfere with insertion of the first connector or pipe and clamp and can be folded into a protection position in a second step.

In one embodiment, the protective elements are walls in the shape of cylindrical portions; such that the protection against the ear of the pipe clamp has an optimized shape, regardless of the orientation of the first connector relative to the second connector.

In one embodiment, the protective elements may overlie the pipe clamp along its entire circumference and form a cylindrical protective ring; whereby complete protection from the ear of the pipe clamp is provided regardless of its angular position.

In one embodiment, the device may further comprise an anti-rotation feature to prevent the first and second connectors from rotating relative to one another about the axis A, preventing any unwanted rotation of the first connector with its pipe relative to the second connector. It is even possible to further provide an indexing of the first connector relative to the second connector and allow easier insertion for the operator by increasing the gripping area.

In one embodiment, the anti-rotation feature may comprise at least one lug arranged on the first connector, said lug being received in a notch formed in the second connector. One can thus further provide an indexing of the first connector relative to the second connector.

In one embodiment, the device may further comprise a mechanism for locking the coupling position by snap-fitting means; whereby any unwanted uncoupling of the connecting device after coupling is prevented, particularly when sterile conditions must be observed.

In one embodiment, the protective elements are at a distance from the outer surface of the pipe. This provides a space to accommodate the ear of the pipe clamp. This also allows adapting to different pipe diameters on different types of first connector, for the same type of second connector attached to a flexible bag or other pipe.

In one embodiment, the pipe clamp is a metal clamp having the general shape of a ring with at least one ear, said ear being intended to be crimped to tighten the clamp. This represents a standard and well known solution for the pipe clamp function.

In one embodiment, the first connector forms a male interface adapted to be received in the second connector forming a female interface; whereby the second connector equipped with protective elements can be obtained relatively easily by molding.

In one embodiment, the first connector may further comprise a gripping tab; whereby an element is provided for a user's fingers to press against, to facilitate insertion of the first connector with assembled pipe into the second connector regardless of the presence of protective elements.

In one embodiment, the second connector may further comprise an identifier such as a barcode or RFID tag placed on the protective elements; whereby it is easy to access information relating to the flexible bag and/or the biopharmaceutical product contained therein, the position on the protective elements being particularly accessible and optimized, which facilitates the tracking process.

According to a second aspect, the invention relates to a connector for fluid connection, adapted and intended for coupling to a complementary connector provided with a tubular nozzle onto which is inserted a flexible pipe with a pipe clamp placed around the end of the pipe in order to clamp the pipe on the tubular nozzle, the connector comprising protective elements which, in the position of coupling with the mating connector, are positioned at least partially facing the pipe clamp in the radial direction, whereby the protective elements prevent the pipe clamp from coming into direct contact with external elements. The invention also relates to a biopharmaceutical bag equipped with at least one such connector for fluid connection.

According to a third aspect, the invention relates to a biopharmaceutical assembly comprising a fluid-connection device as described above.

According to a fourth aspect, the invention also provides a kit of parts comprising the first and second connectors described above, with at least one pipe clamp and optionally a flexible pipe. In addition, the invention relates to an assembly of the above parts into an assembled state with the pipe clamp protected by the protective elements.

According to a fourth aspect, the invention also provides a fluid-connection device intended for connecting a first wall (11) defining a first fluid space (71), in the form of a flexible pipe (11), to a second wall (12) defining a second fluid space (72), in the form of a flexible or rigid disposable enclosure, in a biopharmaceutical assembly comprising:

a connector (8) of plastic material, intended to be connected to the first wall via a tubular nozzle (9) and to the second wall via a collar (28), in order to place the first and second fluid spaces in fluid communication, at least one separate pipe clamp (3), intended to be placed around the end of the pipe (11) in order to clamp the pipe onto the tubular nozzle (9) of the connector, the connector comprising protective elements (4a, 4b) connected to the body (84) of the connector by flexible hinge areas (42), the protective elements being movable between a standby position facilitating insertion of the pipe onto the nozzle and a protection position in which the protective elements are positioned at least partially facing the pipe clamp in the radial direction, whereby the pipe clamp cannot come into direct contact with external elements.

A simple and secure connection for biopharmaceutical assemblies with flexible pipes and enclosures/bags is thus provided.

Advantageously, the protective elements are integrally formed with the body of the connector and the nozzle, in a single molding operation; whereby the connector is inexpensive although incorporating several functionalities.

Advantageously, the axis (W) of the flexible hinges is arranged substantially perpendicularly to the axis of the connector (A).

In one embodiment, the protective elements are formed by two semi-cylindrical walls (4a, 4b) adapted to close onto one another in the protection position to form a generally cylindrical protection around the pipe clamp; whereby a solution is provided that is simple to obtain with a single molding operation, and that is an efficient solution for protecting the clamp.

In one embodiment, the semi-cylindrically shaped protective elements are held in the protection position, once it reached, by a hook or snap-fit system.

BRIEF DESCRIPTION OF THE DRAWINGS

The figures in the drawings will now be briefly described.

Below is a detailed account of several embodiments of the invention, accompanied by examples and with reference to the drawings.

MORE DETAILED DESCRIPTION

In the illustrated example, the flexible pipe 11 is connected to a container 12 containing biopharmaceutical product, by means of a fluid connection device 10 which comprises a first connector 1 and a second connector 2.

The flexible pipe 11 can be generally defined as a first wall 11 defining a first fluid space 71.

The container can be generally defined as a flexible enclosure 12 formed by a second wall defining a second fluid space 72. However, "second wall" could also be understood to mean another flexible pipe (not shown in the figures).

The first connector 1 comprises a tubular nozzle 9 at one end 1a, and a coupling interface 6 for coupling with the second connector at the other end. The first connector further comprises an intermediate portion 7 which will be detailed below.

The tubular nozzle 9 is axisymmetric about the axis A, and the same is true for the coupling interface 6. The coupling interface 6 is a male interface which is provided for insertion into a female interface 20 described further below. Of course, the opposite could be possible, with a male interface in the second connector and a female interface in the first connector, or two genderless connectors.

In the example shown, the male interface 6 in the first connector is generally cylindrical about A, with one or two external grooves for receiving one or two elastomer O-rings 35 for example of silicone.

The intermediate portion 7 comprises a first disk-shaped collar 14 whose usefulness will be apparent below, and a second collar 15 which is also disk-shaped, of larger diameter, the second collar serving as a stop for the pipe insertion. The second collar 15 also supports two gripping members also called gripping "tabs" 18 which facilitate handling when inserting the first connector into the second connector. Specifically, each gripping tab 18 comprises a base portion 18a which extends from the second collar 15, a stiffening rib 18b, and an upper bearing face 18c to support a fingertip.

The tubular nozzle 9 comprises an annular bead 19, which in the example illustrated forms a slight ramp 19a on the side of the flexible pipe to be inserted and a shoulder 19b on the opposite side. The tubular nozzle may comprise a greater number of beads, for example such as the successive notches that are known per se.

One will note that the inside diameter D1 of the tubular nozzle 9 is substantially close to the inside diameter of the flexible pipe 11 at rest.

When the flexible pipe 11 is threaded onto the tubular nozzle 9, the pipe is deformed radially outward by the ramp shape 19a, then as it is further inserted it returns to a narrower diameter at the cylindrical bearing surface 9a.

Figures 1, 2:
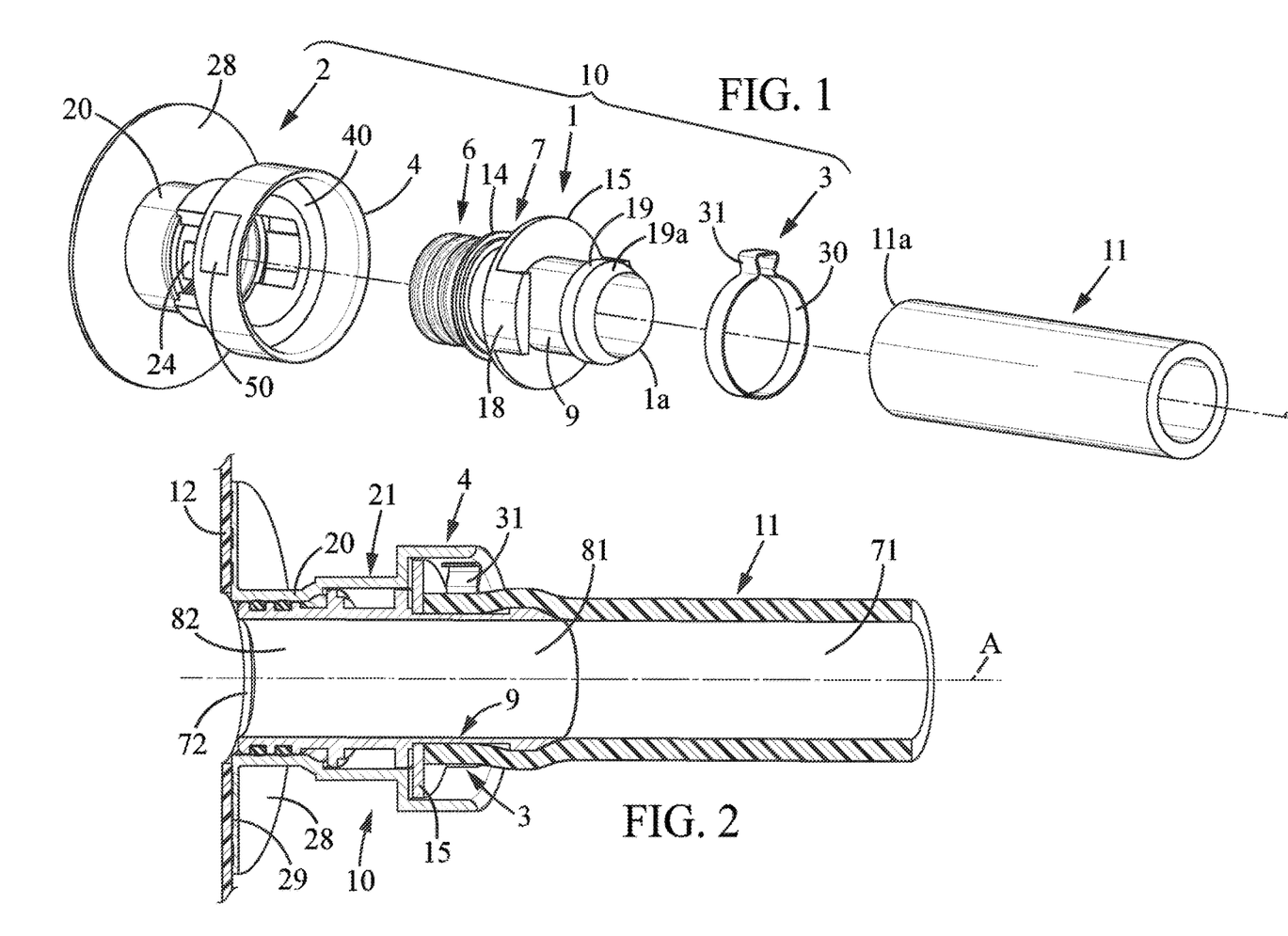
FIG. 1 is an exploded view of the connection device according to the invention.
FIG. 2 is an axial sectional view of the connection device of FIG. 1, in the coupled position, along section line II-II visible in FIG. 4.
Figure 3:
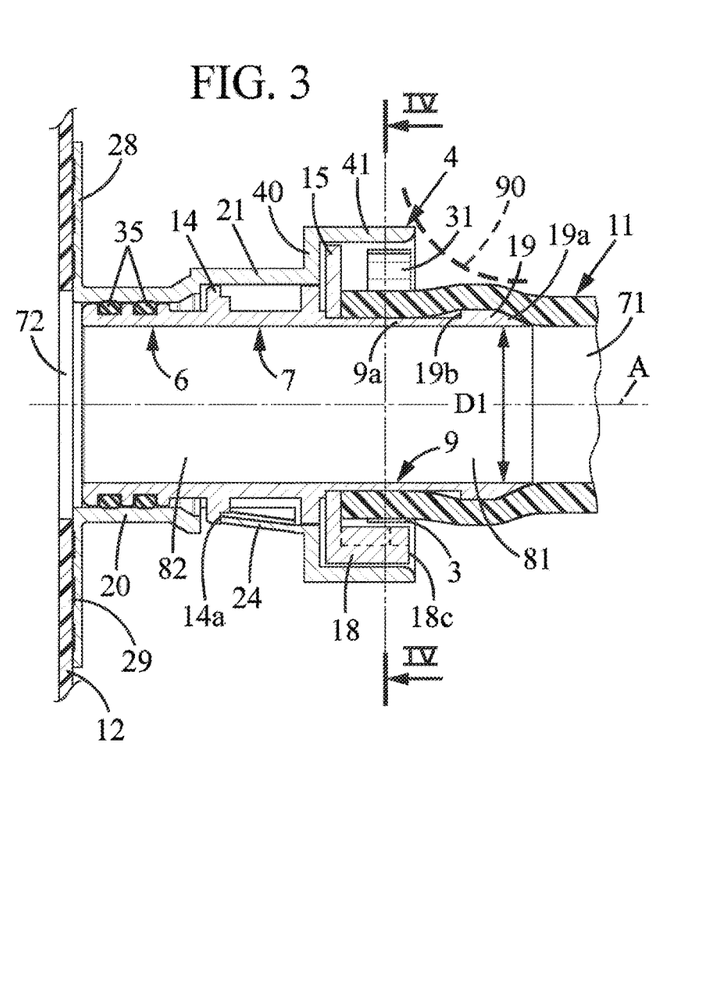
FIG. 3 is a more detailed sectional view of the connection device of FIG. 1, in the coupled position, along section line III-III visible in FIG. 4.

The insertion may continue until the forward end of the pipe 11a comes to bear against said second collar 15 (see FIGS. 2 and 3).

Once the flexible pipe is inserted onto the tubular nozzle 9, at least one pipe clamp 3 is placed around the pipe at said bearing surface 9a. It should be noted here that the pipe clamp 3 may be readied beforehand, being placed around a rear portion of the pipe prior to the insertion process.

Once the clamp is in the proper position around the bearing surface of the tubular nozzle, the clamp is tightened.

Figure 4:
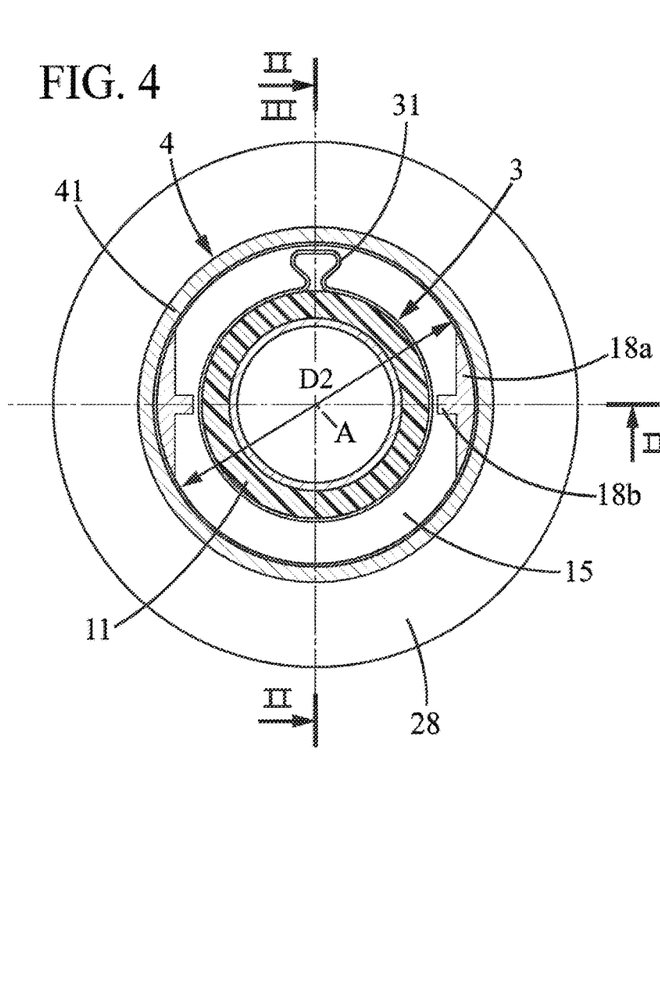
FIG. 4 is a detailed cross-section of the connection device of FIG. 1, in the coupled position, along section line IV-IV visible in FIG. 3.

The pipe clamp shown in the figures is a metal clamp with only one ear 31 provided for tightening. However, there could be more than one ear. The clamping ear 31 is preferably positioned at an angular distance from each of the gripping tabs 18 (see FIG. 4).

Pliers are used for example to crush the ear shape 31 so as to reduce the diameter of the ring 30 formed by the pipe clamp 3. As a result, the pipe clamp then has a smaller diameter than the outer surface of the flexible pipe at rest, and therefore exerts a radial force directed inward.

This radial force has two objectives: the first is to ensure a sufficient seal between the pipe 11 and the tubular nozzle 9, and the second is to hold the pipe around the nozzle mechanically in order to prevent the pipe from detaching from the tubular nozzle when pulled, this second objective being achieved primarily due to said shoulder 19b.

It should be noted that it is possible to use two adjacent clamps for the clamping function. It should also be noted that metal clamps without ears can be used (low-profile crimped clamps).

The second connector 2 comprises a collar 28 for attachment to the flexible bag 12, such attachment usually being achieved by one or more welds 29. The collar 28 is flat and presses against a large surface area of the bag 12. The center of the collar 28 is open to provide fluid communication between the inner cylindrical space 82 of the second connector and the inner space 72 of the bag.

In addition, the second connector 2 comprises a tubular region 20 forming the female coupling part and receiving the abovementioned male interface 6; in the coupled position, the abovementioned O-rings 35 are pressed inwardly by the inner cylindrical surface of the tubular region 20 forming the female interface. A sealed fluid connection between the first connector 1 and the second connector 2 is thus obtained.

In addition, the second connector 2 comprises a body 21 which extends from the tubular region 20 in a direction away from the collar 28.

The body 21 is bell-shaped around axis A, with a middle portion comprising locking tabs 24, here two in number although there may be any number, and adjacent to the open end, a cylindrical portion 41 of larger diameter D2 which forms protective elements 4 whose function will be detailed below.

As can be seen in FIGS. 2 and 3, the second collar 15 is received within the wide cylindrical portion of diameter D2, until it reaches the base 40 of this portion in the coupling position, thus providing a stop to end the movement of inserting the first connector into the second connector.

The outer rim 41 of the wide cylindrical portion of diameter D2 forms the so-called "protective elements" for the pipe clamp 3: in the coupling position this clamp lies within the internal area defined by said cylindrical portion 41. In this manner, if during manipulation or movement of the connection device, said device can come into contact with external elements 90, then it is not the pipe clamp which will come into contact with said external elements 90 but instead it will be the protective elements 4, here the outer rim 41 of the cylindrical portion, which will come into contact with the external element or elements 90 (see FIG. 3).

Thus, all damage due to contact with a damaging portion of the collar 3 can advantageously be avoided.

It should be noted that "protective elements" can be understood to mean any shape which can be interposed between the pipe clamp 3 and the external elements 90. In particular, it is not necessary for the protection to form a continuous ring as in example shown: there could be a plurality of disjoint tabs distributed along the circumference, or a plurality of walls in the form of disjoint cylindrical portions distributed along the circumference. Advantageously, the protective elements are integrally obtained when molding the second connector, in other words the protective elements come from the material of the body 21 of the second connector 2.

In another variant embodiment not shown, the protective elements 4 may be formed from a separate part that is snap-fitted onto the body 21 of the second connector, for example in the axial direction.

The first and second connectors 1,2 may be obtained by molding a plastic, for example polypropylene, polyethylene, polycarbonate, or polysulfone.

According to one optional aspect, locking tabs 24 may be provided in the body 20 of the second connector. These locking tabs 24, of which there are two in the example illustrated, are flexible, and move apart outwardly when the first collar 14 reaches their free end and then return inwardly to be positioned facing a removal-prevention stop 14a at the rear of the first collar 14. After this, it is impossible to reverse the movement, meaning to remove the first connector from the second connector, without first eliminating the locking tabs 24 in some manner.

The materials of the first and second connectors may be of different colors, which makes it easy to verify visually that the locking tab 24 is positioned correctly against the first collar 14.

Note that the first connector 1 defines a first hollow passage 81 intended to be placed in fluid communication with the first fluid space 71. Similarly, the second connector defines the second hollow passage 82 already mentioned, intended to be placed in fluid communication with the second fluid space 72 (the interior of the plastic bag in the specific case illustrated).

Figure 6:
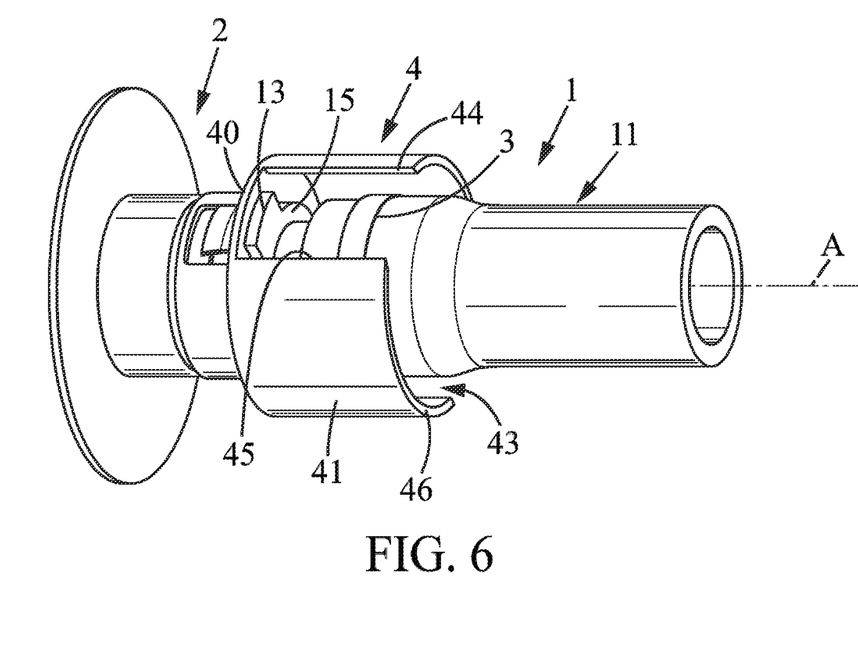
FIG. 6 shows an alternative embodiment comprising an anti-rotation feature.

According to an optional characteristic, illustrated in FIG. 6, the connecting device 10 may include an anti-rotation feature to prevent the first connector 1 from rotating relative to the second connector 2 about axis A. More specifically, this is for example a radial lug 13 arranged on the first connector, for example at the second collar 15. This lug 13 is received in a notch 43 formed in the rim 41 of the bell shape 4 which forms the protective elements of the clamp. In the illustrated example, there are two diametrically opposed lugs 13 which are each received in a respective notch 43.

Each notch 43 is delimited by a first axial edge 44 and a second axial edge 45 which each run from the base 40 to the front end 46 of the protective elements 4.

This configuration facilitates the motion of inserting the first connector executed by a user who grasps it at the lugs; he can push the lugs 13 in said notches 43 until the first collar 15 touches the radial base 40 of the protective elements. This configuration also limits the rotation of the first connector 1 inside the second connector 2.

Figures 5, 5A:
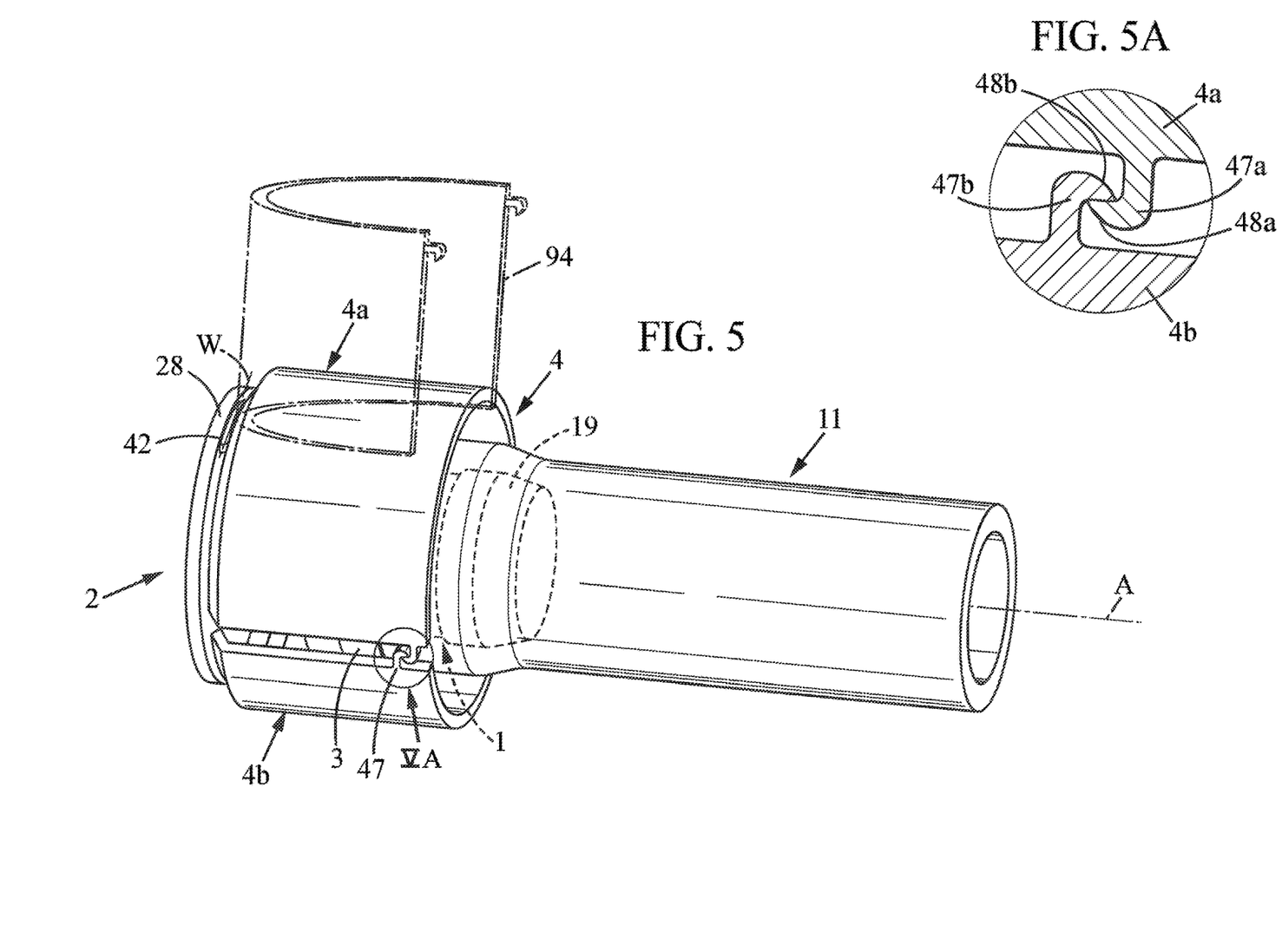
FIGS. 5 and 5A show a variant embodiment in which the protective elements for the hinge are arranged on the body of the second connector by means of flexible hinge areas.

In an alternative embodiment shown in FIG. 5, the protective elements 4 are not formed rigidly relative to the body 21 of the second connector but are connected thereto by flexible hinge areas 42. For example, there may two half-shells 4a, 4b, which are initially open so as not to interfere with insertion (only half shell 4a is represented in this initial position, shown in phantom lines 94 in FIG. 5); after insertion, said two half-shells are pivoted towards each other (half shell 4a rotates about axis W), to snap-fit onto one another by means of locking shapes 47. The hooks may be complementary elastic hooks, denoted 47a, 47b in FIG. 5A; the complementary ramps 48a, 48b combined with the elasticity of the hook stems allow automatically locking at closure.

Any other equivalent form of hooks or snap-fitting means are equally possible for retaining the two half-shells in a position where together they form the protective elements 4 preventing external elements 90 from coming into direct contact with the collar 3.

Figure 7:
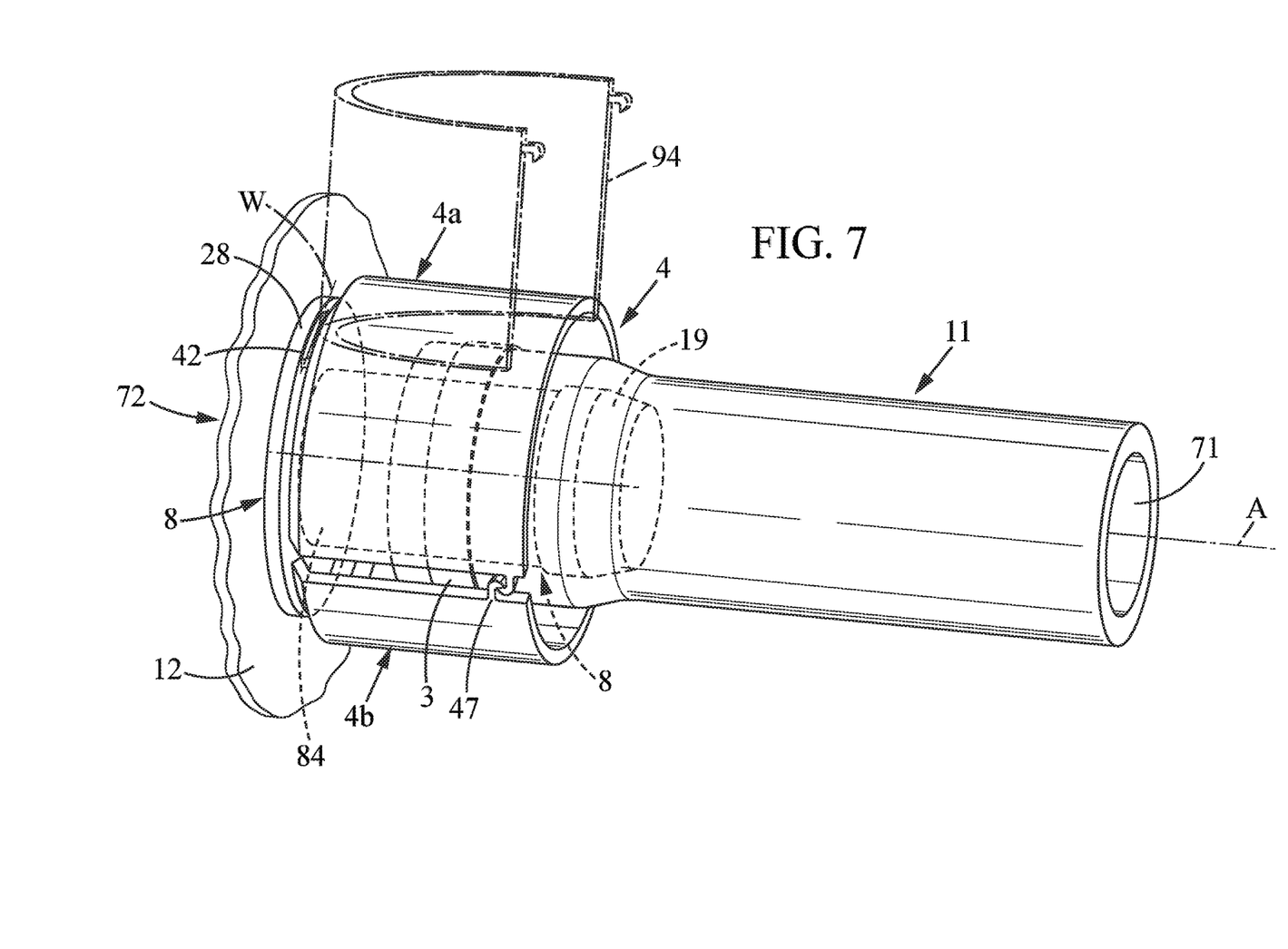
FIG. 7 is similar to FIG. 5 and represents another variant embodiment.

According to a variant represented in FIG. 7, the first connector 1 and the second connector 2 are formed as a single piece 8, in a context where the flexible pipe 11 is connected more or less permanently (single use) to a bag or enclosure 12, the flexible pipe and the bag/enclosure being identical or similar to what was described above. The pipe clamp 3 is similar in form and function to what was described above.

The connector 8 is a plastic piece integrally obtained by molding, the connector comprising a body 84, a tubular nozzle 19 similar or identical to what was described above, and a collar 28 for attachment to the bag, similar or identical to what was described above with reference to FIGS. 1-6.

In addition, the connector comprises protective elements 4a, 4b connected to the body 84 of the connector by flexible hinge areas 42. In the illustrated example, the protective elements are formed by two semi-cylindrical walls intended to come together into a protection position to form a generally cylindrical protection around the pipe clamp, as has already been described with reference to FIG. 5.

Advantageously, the protective elements can be moved between a standby position (in dotted lines 94 in FIG. 7), facilitating the insertion (manual or automatic) of the pipe onto the nozzle, and a protection position (solid line in FIG. 7) in which the protective elements are positioned around the pipe clamp 3.

Advantageously, the axis W of the flexible hinges is arranged substantially perpendicularly to the axis of the connector A.

Advantageously, the protective elements of semi-cylindrical shape are retained in the locked position, once this is reached, by a hook or snap-fit system 47 already discussed above in the description for FIG. 5A.

Preferably, the protective elements 4a, 4b are in the standby position by default, and moving them to the protection position requires overcoming moderate elastic restoring force. Thus, the pipe can be directly inserted without prior preparation or precautions, and without interference by the protective elements. In a second step, the protective elements are brought towards each other and automatically hook together to form an effective protection of the clamp.

In addition, an optional characteristic is provided that is compatible with all variants mentioned above: this concerns the integration of an identifier 50, such as a barcode or electronic tag, for example an RFID tag. This identifier is provided in the first connector 1 or the second connector 2, more preferably on the protective elements 4 which are easy to access from the outside. It is thus easy to read the data by means of a reading tool.

In the case of an RFID tag, this may be positioned at any location, namely the first connector or the second connector, with no need for a line of sight.

The invention claimed is:

1. A Fluid-connection device configured for connecting a first wall defining a first fluid space, in the form of a flexible pipe, to a second wall defining a second fluid space, in the form of a pipe or an enclosure that is flexible or rigid and disposable, in a biopharmaceutical assembly, for ensuring fluid communication between the first fluid space and the second fluid space, comprising:
   a first connector defining a first hollow passage and configured for connection to the first wall and in fluid communication with the first space,
   a second connector defining a second hollow passage and configured for connection to the second wall and to be in fluid communication with the second space,
   the first connector and the second connector being of plastic and being configured to be coupled together in a relative coupling position, along an axis A,
   the first connector comprising a tubular nozzle configured for insertion into one end of the pipe, and a front coupling portion,
   at least one separate pipe clamp, separate from the first connector and the second connector and configured for placement around the end of the pipe in order to clamp said pipe onto the tubular nozzle of the first connector,
   the second connector comprising a protective element which, in the relative coupling position with first connector, is positioned so as to the least partially face the pipe clamp in a radial clamp in a radial direction, and configured so that the clamp cannon come into direct contact with external elements,
   wherein the protective element is configured to be integrally formed from a body of the second connector so that said body of the second connector and said protective element form a monolithic one-piece element.

2. The device according to claim 1, wherein the protective element is connected by flexible hinge areas to the body of the second connector.

3. The device according to claim 2, wherein the pipe clamp is a metal clamp having the general shape of a ring with at least one ear, said ear being intended to be crimped to tighten the clamp.

4. The device according to claim 2, wherein the first connector further comprises a gripping tab.

5. The device according to claim 1, wherein the protective element is a wall in the shape of a cylindrical portion.

6. The device according to claim 1, wherein the protective element overlies the pipe clamp along an entire circumference and forms a cylindrical protective ring.

7. The device according to claim 1, further comprising an anti-rotation feature to prevent the first and second connectors from rotating relative to one another about the axis A.

8. The device according to claim 7, wherein the anti-rotation feature comprises at least one lug arranged on the first connector, said lug being received in a notch formed in the second connector.

9. The device according to claim 1, further comprising a mechanism for locking the relative coupling position by snap-fitting.

10. The device according to claim 1, wherein the protective element is at a distance from the outer surface of the pipe.

11. The device according to claim 1, wherein the pipe clamp is a metal clamp having the general shape of a ring with at least one ear, said ear being configured to be crimped to tighten the clamp.

12. The device according to claim 1, wherein the first connector forms a male interface configured to be received in the second connector (2) forming a female interface.

13. The device according to claim 1, wherein the first connector further comprises a gripping tab.

14. The device according to claim 1, wherein the second connector further comprises an identifier comprising a barcode or radio frequency identification tag placed on the protective element.

15. A Biopharmaceutical assembly comprising a fluid-connection device according to claim 1.

16. The fluid-connection device according to claim 1, wherein the protective element is configured to be integrally formed from a body of the second connector so that said body of the second connector and said protective element is integrally obtained by a single molding operation.

17. The fluid-connection device according to claim 1, wherein the protective element is adjacent to an open end of said body of second connector and includes a cylindrical portion of larger diameter than a diameter of said body of second connector,
and wherein a length along said axis A of said cylindrical portion of larger diameter is smaller than a length along said axis A of said body of second connector.

18. The fluid-connection device according to claim 1, wherein said first connector also comprises a male coupling interface at a first end of said first connector opposite to a second end of said first connector at which is located said tubular nozzle,
wherein said second connector also comprises a tubular region forming a female coupling part, said male coupling interface of said first connector being provided for insertion into said female coupling part of said second connector,
wherein said male coupling interface has at least one external groove for receiving at least one elastomer O-ring,
and wherein said at least one elastomer O-ring is pressed inwardly by an inner cylindrical surface of said tubular region, so as to form a sealed fluid connection between said first connector and said second connector.

19. The fluid-connection device according to claim 1, wherein said second connector comprises a flat collar for attachment to a flexible bag.

* * * * *